(12) United States Patent
Ding et al.

(10) Patent No.: US 7,297,312 B2
(45) Date of Patent: Nov. 20, 2007

(54) SIMULTANEOUS MULTIANALYTE ELECTROCHEMICAL ASSAY BASED ON SPATIAL RESOLUTION

(75) Inventors: Ying Ding, Mason, OH (US); Brian Halsall, Cleves, OH (US); William R. Heineman, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 335 days.

(21) Appl. No.: 09/268,437

(22) Filed: Mar. 12, 1999

(65) Prior Publication Data

US 2001/0029048 A1    Oct. 11, 2001

Related U.S. Application Data

(60) Provisional application No. 60/078,162, filed on Mar. 16, 1998.

(51) Int. Cl.
*G01N 27/00* (2006.01)

(52) U.S. Cl. .................. 422/82.01; 422/82.02; 422/82.03; 422/50; 422/90; 422/98; 435/6; 435/7.1; 435/7.4; 435/7.92; 435/971; 435/973; 436/524; 436/525; 436/149

(58) Field of Classification Search .......... 422/82.01, 422/82.02, 82.03, 50, 68.1, 90, 98; 435/6, 435/7.1, 7.9, 7.92, 93, 94, 95, 971, 973, 176, 435/285.2, 288.4; 436/525, 806, 524, 149
See application file for complete search history.

(56) References Cited

U.S. PATENT DOCUMENTS

| 5,830,680 | A |   | 11/1998 | Meyerhoff et al. | ......... 435/7.92 |
| 5,851,840 | A | * | 12/1998 | Sluka et al. | ................ 436/525 |
| 5,981,203 | A | * | 11/1999 | Meyerhoff et al. | ......... 435/7.92 |
| 6,066,448 | A | * | 5/2000 | Wohlstadter et al. | .......... 435/6 |
| 6,140,045 | A | * | 10/2000 | Wohlstadter et al. | .......... 435/6 |

OTHER PUBLICATIONS

Ducey et al., Competitive nonseparation electrochemical enzyme binding/immunoassay for small molecule detection, Analytica Chemica Acta 357 (1-2): 5-12 (1997), Abstract Only.*
Merriam-Webster medical Dictionary, http//ww2.merriam Webster.com/cgi-bin/mwmednlm?book= Medical &va=analyte, printed Mar. 7, 2007.*

* cited by examiner

*Primary Examiner*—Gailene Clare R. Gabel
(74) *Attorney, Agent, or Firm*—Wood, Herron & Evans, L.L.P.

(57) ABSTRACT

A simultaneous multianalyte electrochemical assay includes a cell which has a surface and the surface includes analyte binding sites i.e., antibodies or antigens on a solid phase at distinct separate locations. Separate working electrodes are located within proximity to these separate locations. Enzyme labeled antibodies or antigens depending on the assay format are added and the enzyme reaction product measured, by simultaneous amperometric measurement with the independent electrode in each area. The electrodes are spatially separated from adjacent analytes so that a measurement can be taken before cross-interference due to diffusion of product from adjacent analyte areas.

6 Claims, 1 Drawing Sheet

SIMULTANEOUS MULTIANALYTE ELECTROCHEMICAL ASSAY BASED ON SPATIAL RESOLUTION

Applicant claims priority to application Ser. No. 60/078,162 filed Mar. 16, 1998, now abandoned.

BACKGROUND

Simultaneous multianalyte binding assay (SMBA), in which two or more analytes are measured simultaneously in a single assay, represents the next major advance in binding assay methodology. SMBA is important because it uses less sample, the test throughput is increased, and the overall cost per test is decreased. The first SMBA, in which human insulin and growth hormone in serum were measured using two different radioisotope labels was reported in 1966. Since then, various approaches for SMBA have been demonstrated. Many of these involve the use of multiple labels, such as radioisotopes and fluorophores. Other ways of performing SMBA include a microspot assay, a method based on spatially distinct fluorescent areas quantitated by laser-excited solid-base time-resolved fluorometry, and a nonseparation electrochemical enzyme immunoassay using multiple gold films deposited on the same membrane.

Electrochemistry is one of the most sensitive analytical methods, and has been shown to be an effective technique for detection in immunoassay. The assay is based on labels that are either electroactive or catalyze the production of an electroactive product. Electrochemical immunoassay has many features in common with other types of binding assays and one that is less well shared, but very important, in that it can be miniaturized easily. This is especially important in the development of disposable devices and methodology for ultra-small sample amounts. The potential exists to develop simple electrochemical binding assay kits for applications that require small, portable systems.

A simultaneous dual-analyte immunoassay method based on releasable metal ion labels is known. That approach, however, is not generic due to the fact that a different metal label is needed for each analyte, and the detection limit was higher than with enzyme labels.

SUMMARY OF THE INVENTION

The present invention is premised on the realization that a single electrochemical binding assay device can be used to determine multiple analytes in a single sample by simultaneous amperometric measurements using a plurality of working electrodes.

More particularly the present invention is premised upon the realization that by establishing different analyte binding sites i.e., antibodies or antigens on a solid phase at a distinct separate location and locating separate working electrodes within proximity of those separate locations, one can add enzyme labeled antibodies or antigens depending on the assay format, and then quantitate the amount of enzyme reaction product, whether chemically the same or different, generated by simultaneous amperometric measurement with the independent micro electrode for each area. The independent micro electrode for each area is spatially separated from adjacent analyte so that a measurement can be taken before cross-interference due to diffusion of product from adjacent analyte areas. The objects and advantages of the present invention will be further appreciated in light of the following detailed descriptions and drawings in which:

DETAILED DESCRIPTION

Figure 1:
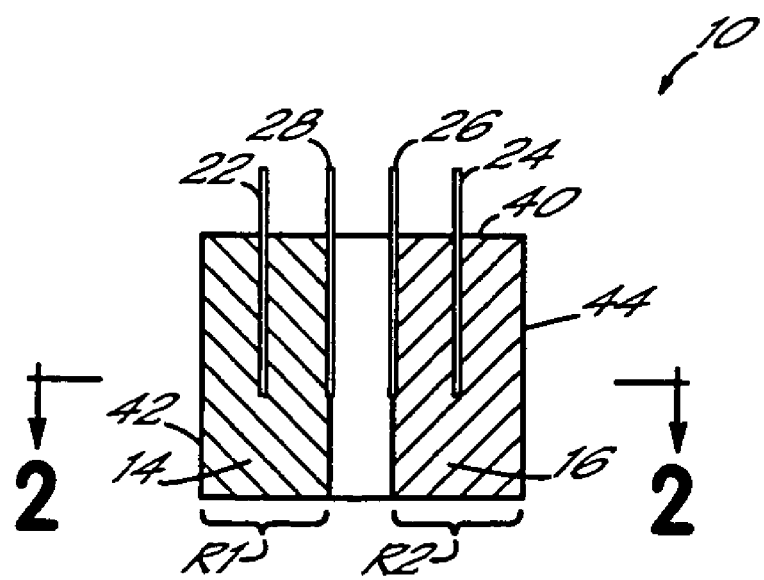
FIG. 1 is a diagrammatic depiction of the present invention.
Figure 2:
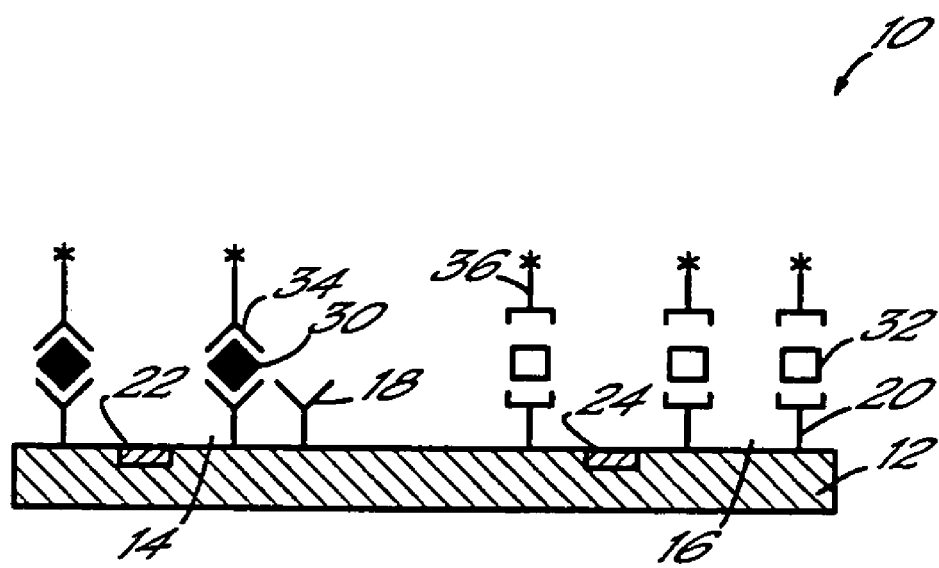
FIG. 2 is a cross-sectional view taken at lines 2-2 of FIG. 1.

The invention is diagrammatically depicted in FIGS. 1 and 2. The electroanalytical cell 10 of the present invention includes a substrate 12, such as polystyrene or the like which has a first 14 and a second area 16 coated with different analyte binding sites depicted as 18 and 20 in FIG. 2. Area 14 for example can be coated with a first antibody 18 and area 16 coated with a second antibody 20 as depicted in FIG. 2. A first working electrode 22 is located on the area 14 and a second working electrode 24 is positioned on area 16 with the common reference and auxiliary electrodes 26 and 28 separated from the two working electrodes.

In use a liquid solution potentially containing quantifiable amounts of a first and second analyte 30 and 32 (see FIG. 2) which are adapted to bond to the first and second binding areas would coat the substrate 12 and the respective analytes 30 and 32 allowed to bind to the binding sites 18 and 20. A solution containing analyte specific enzyme labeled antibodies or enzyme labeled antigens 34 and 36 depending upon the assay format used would be added and would bind to the respective analytes specific regions. Substrates for the enzyme labels would then be added. The general procedure may also include appropriate steps to rinse the device or portions thereof.

The working electrodes 22 and 24 would then simultaneously, or in any sequence if done sufficiently rapidly, measure the amount of enzyme reaction product generated in each area. The first working electrode 22 is separated from the second analyte binding site 16 by a sufficient distance that the reaction product from the enzyme labeled antibody 36 will not diffuse in sufficient quantity to interfere with the first working electrode 22 in a quiescent solution without active mixing (i.e., quiescent relative to the speed of measurement) before a measurement is taken of the first analyte present. The closest distance between a working electrode and an adjacent analyte area is estimated using the Einstein equation:

$$d = \sqrt{2Dt}$$

Where d is the distance in centimeters that the product will move on the average, D is the Fickian diffusion coefficient expressed as $cm^2/s$ and t would be time in seconds before which the measurement is taken. Thus this estimates the minimum distance from electrode 22 to antibody 20 and likewise the distance from antibody 18 to electrode 24 assuming the measurement is taken at t seconds.

The method used to form the binding sites 14 and 16 will of course vary depending on the substrate 12, the composition of 18 and 20, and the analyte. These methods are very well known having been used for many different binding assays.

The binding sites can be formed from any molecule which can be bound to a substrate and which will specifically bind to a desired analyte. Specific binding sites include ionophores, cofactors, polypeptides, proteins, glycoproteins, enzymes, immunoglobulins, antibodies, antigens, lectins, neurochemical receptors, oligonucleotides, polynucleotides, molecules of DNA, molecules of RNA, active fragments or subunits or single strands of the preceding molecules, specific binding polymers and mixtures thereof. Obviously the analytes will be specifically complementing compounds.

The label can be another specific binding molecule or an analyte molecule depending on the assay format with the addition of a detectable compound such as alkaline phosphatase, glucose-6-phosphate dehydrogenase, catalase, horseradish peroxidase, glucose oxidase, glucose dehydrogenase, NADH oxidase, uricase, urease, creatininase, sarcosine oxidase, creatinase, creatine kinase, creatine amidohydrolase, cholesterol esterase, cholesterol oxidase, glycerol kinase, hexokinase, glycerol-3-phosphate oxidase, lactate dehydrogenase, alanine transaminase, aspartate transaminase, amylase, lipase, esterase, gammaglutamyl transpeptidase, L-glutamate oxidase, pyruvate oxidase, diaphorase, bilirubin oxidase, laccase, tyrosinase and their mixtures.

Although a typical test cell will include many different binding sites and labels, the detectable compound on the label in the preferred embodiment should be the same for all labels.

Further where the label includes an enzyme, excess enzyme substrate must also be added. Compounds which can be detected using the present invention include:

Therapeutic and non-Therapeutic drugs; metabolites: Theophylline, phenytoin, carbamazepine, ethosuximide, phenobarbital, pyrimidine, caffeine, digoxin, digitoxin, lidocaine, n-acetylprocainamide, procainamide, quinine, amikacin, chloramphenicol, gentamicin, tobramicin, netilmicin, vancomycin, amitriptyline, imipramine, desipramine, thyroxine, acetaminophen, amphetamine/methamphetamine, barbiturate, benzodiazepine, cannabinoid, cocaine, ethaqualine, methadone, methotrexate, opiate, phencyclidine, propoxyphene, salicylate, estriol, estradiol, testosterone, aldosterone, androstenedione, cortisol, and prostaglandin.

Microorganisms, including viruses: Rubella, Paramyxoviruses, (Influenza Mumps, Measles, Respiratory Syncytial Virus), Cytomegalovirus, Adenovirus, Rotavirus, Retrovirus (Friend Leukemia Virus, Radiation Leukemia Virus, Human Immunodeficiency Virus), Hepatitis A, Hepatitis B, Infections Mononucleosis, Epstein-Barr Virus, Papillomavirus, *Mycoplasma pneumoniae, Toxoplasma, Giardia, Amebiasis, Salmonella, Streptococci* and Anti-Streptolysin O, *Legionella, Staphylococci, Hemophilus, Neisseria, Chlamydia, Treponema, Candida, Histoplasma, Blastomycosis, Cryptococcus* and *Coccidia*.

Macromolecular analytes: IgE total, allergen specific IgE, C-reactive protein, IgG, IgM, IgA, IgD, (and fragments), adrenocorticotrophic hormone, alpha-fetoprotein, human growth hormones and variants, human chorionic gonadotropin, human luteinizing hormone, follicle-stimulating hormone, T4, T Uptake, T3, total thyroxine, thyroid-stimulating hormone, human leukocyte antigen (HLA), Factor III, von Willebrand's, fibrinogen/fibrin degradation products, blood group surface antigens, HLA antigens, platelet Factor IV, and others, double-stranded DNA, single-stranded DNA, rheumatoid factor, Smith antigen, Smith antigen/ribonucleoprotein, immune complexes, Apo A-1, Apo A-II, Apo B, Apo C-II, Apo C-III, Apo E, HDL, LDL, VLDL, alpha 1 acid glycoprotein, acid phosphatase, carcinoembryonic antigen, prostate specific antigen, CPK BB, alpha I antitrypsin, alpha 2 antiplasmin, beta 2 microglobulin, ferritin, transferrin and ceruloplasmin.

These listings should be construed as illustrative, not exclusive. Although the examples show an amperometric detection, basically any electrochemical technique which utilizes an electrode can be used. For example, electrochemical techniques where potential is controlled and current is measured such as chronoamperometry, cyclic voltammetry, linear scan voltammetry, pulse voltammetry, and differential pulse voltammetry can be used. Further techniques in which potential is controlled and charge is measured work in the present invention, for example, chronocoulometry. Techniques in which current is controlled and potential and/or time are measured such as chronopotetiometry can also be used as well as spectroelectrochemical techniques such as electrochemiluminescence, and internal reflection spectroelectrochemistry.

EXAMPLES

A macroscopic prototype dual working electrode according to the present invention was fabricated to study the fundamental aspects of the present invention. The cell was made of Teflon and is shown as FIG. 1. It consists of two gold wires 0.25 mm diameter as working electrodes 22 and 24. One silver-silver chloride wire reference electrode 26 and one platinum wire (0.25 mm/diameter) auxiliary electrode 28 the silver-silver chloride electrode was a silver wire with silver chloride electrolytically deposited on the electrode by anodization in 0.1 molar HCl. Both working electrodes share the reference and auxiliary electrodes. Four electrodes were inserted through small holes in the side wall 40 of the cell. Antibody 18 and 20 was immobilized on a piece of polystyrene sheet 12 which forms the bottom of the cell 10. The electrodes rest on the polystyrene sheet 12 which is liquid impervious leaving no gap in between. The distance between two adjacent electrodes 22 and 24 was 2.5 mm. Both the assay and electrochemical detection were carried out in the cell which had a volume of 150 micro liters. As discussed below, the same antibody was used for both the first and second analyte area 14 and 16 purely for these test purposes. The specific antibody was anti-mouse IgG. The enzyme label was alkaline phosphatase (alp). The enzyme substrate was para amino phenyl phosphate (PAPP) and the enzymatic reaction product was para amino phenol (PAP).

A 179 TRMS digital multimeter was used to measure the reference electrode's potential. A dual potentiostat system was set up by connecting two BAS LC-4C detectors together. Each LC-4C controls the potential and measures the current of its assigned working electrode independently. The current signals were recorded by a strip chart recorder. To prepare the cell, the piece of polystyrene was positioned in the bottom of the cell with double-sided tape. The cell was washed with methanol and water and the electrodes were slid into position and cleaned electrochemically.

Two hundred μl of labeled antibody (Ab*) solution were pipetted into the cell (filling the cell above the electrodes), incubated for 12 h at 4° C., and removed by aspiration. After rinsing with tris buffer three times, 200 μl of PAPP solution were added to the cell, and the enzymatic reaction was allowed to proceed in the dark for 20 min. For blank experiments, the acetate buffer with no Ab* was incubated for 12 h, and then the same procedure was followed.

The dual-potentiostat was turned on to record the current signals every 2 or 5 min. after substrate addition for a total time of 20 min. Both working electrodes were held at +300 mV vs the reference electrode. At 10 s after turning on the dual-potentiostat, the current signals at the two working electrodes were recorded. The dual-potentiostat was then turned off until the next measurement was to be made.

A freshly-cut polystyrene piece 12 was fixed in the cell 10, 50 μl Ab* (0.045 μg ml$^{-1}$) were pipetted into region 14, covering the area from the auxiliary electrode to the left side of the cell-wall 42. The auxiliary electrode acted as a barrier to prevent solution from leaking away to other areas. Another 50 μl of 0.0225 μg ml$^{-1}$ conjugate were pipetted into region 16, covering the area from the reference electrode 26 to the right side of the cell-wall 44. The reference electrode acted as a barrier at the right side (FIG. 2). The solution connection of the cell is provided by the addition of 200 μl PAPP solution during the detection step, filling the cell above the electrodes and removing their barrier function. The incubation step and detection procedures were the same as stated above.

Example 1

Cross Interference

Since this method is based on the continuing resolution of the PAP generated for each analyte, measurement has to be taken before cross-interference due to PAP Fickian diffusion to the working electrode for the other analyte can occur. Convection must be minimized. The Einstein equation can be used to calculate the distances molecules move by diffusion. For a diffusion coefficient (D) of 10$^{-5}$ cm$^2$ sec$^{-1}$, the maximum distance that PAP molecules on the average can travel in a quiescent solution in 20 min. is 1.5 mm. The electrodes in this cell and the edges of the Ab immobilization regions were 2.5 mm apart, which should be enough to avoid cross-interference with Fickian diffusion as the only mode of mass transport.

A PAP diffusion experiment was conducted to test this conclusion. A solution of PAP was added to the cell, electrode 22 was held at +300 mV so that PAP was oxidized under diffusion-controlled conditions, and electrode 24 was held at −200 mV, at which potential oxidized PAP would be reduced. PAP oxidized at electrode 22 would diffuse away, and its arrival at electrode 24 would be signaled by an increase in reduction current. There was no noticeable increase in reduction current within 60 min., indicating that oxidized PAP had not yet diffused to electrode 24 in detectable quantity. Therefore, during the course of amperometric measurement, the product formed at one electrode has not reached the other working electrode 20 min. after the addition of enzyme substrate, and the measurements can be cross-interference-free.

Example 2

Analyte Quantitation

Chronoamperometry was used to detect enzyme-generated PAP. Other techniques could be used as well, but due to the convenience and availability of the BAS dual-potentiostat, chronoamperometry was used here. In this method, the current measured is a function of time, the concentration of electrochemically active species and other factors. These are embodied in the Cottrell equation:

$$i_t = \frac{nFAC^\circ \sqrt{D}}{\sqrt{\pi t}}$$

where $i_t$=current at time t, amperes; D=diffusion coefficient, cm$^2$ s$^{-1}$; A=electrode area, cm$^2$; F=Faraday's constant, 96485 C eq$^{-1}$; C$^\circ$=concentration of species being detected, mol cm$^{-3}$, t=time, sec. If t is fixed, $i_t$ varies linearly with C$^\circ$. Although this equation is for a planar electrode, nonplanar electrodes such as the wire electrode used in this method will obey it at sufficiently short times since the curvature of the electrode surface is then negligible relative to the depth of the diffusion layer. Based on a Cottrell plot (it$^{1/2}$ vs t) for this electrochemical detection system, under the experimental conditions, the available time window during which it$^{1/2}$ is a constant with respect to t for Cottrell measurements of this system is between 8 and 100 s. The large positive deviation of it$^{1/2}$ at t<8 is likely due to the slow charging of the electrode double layer during the potential step. The positive deviation at t>100 s can be a result of nonplanar diffusion and/or convection in the cell. The current signals taken in this time window will have a linear relationship with the concentration of electroactive species. The earlier the measurements are taken, the larger the current signals, and therefore, the more sensitivity the detection will have. However, it should be realized that the time window used above relates to the exemplary experiment and should not be construed as defining the limits of the method. It is to be anticipated that the time window may change depending on the electrode material and size, for example.

Current-concentration plots for PAP at both working electrodes using this method with the current measured at 10 s showed a slight difference between the two working electrodes in the concentration range of 0-2 mM.

Example 3

Simultaneous Detection of Dual Analytes

The concept of the spatial resolution dual binding assay is based on being able to do separate binding assays in the two regions of the electrochemical cell. This was evaluated with three types of experiments.

First it was established that Ab* could be passively immobilized on polystyrene. Identical concentrations of the same Ab* were immobilized in the two regions 14 and 16. Substrate was then added and the signals at electrodes 22 and 24 were recorded. The detection signals at both electrodes 22 and 24 increase with time as PAP concentrations increase in each region, which is the expected result if Ab* has been immobilized.

Different concentrations of enzyme label in the two regions could also be detected. A volume of 0.045 μg ml$^{-1}$ of Ab* was immobilized around electrode 22 and 0.0225 μg ml$^{-1}$ of Ab* around electrode 24. Since the concentration of Ab* at electrode 22 was twice that at electrode 24, it was expected that the enzymatic reaction rate at electrode 22 would be twice that at electrode 24, and that the $di_1/dt$ would also be twice that of $i_2$. The results demonstrate that the signals associated with each individual zone can be quantitated simultaneously. In actual cells two antibodies $Ab_1$ and $Ab_2$ would be used as well as two labeled antibodies $Ab_1$* and $Ab_2$* but the labels would be the same.

The invention has been demonstrated with a dual working electrode electrochemical cell with the capture antibody for each analyte immobilized adjacent to each detecting electrode. In this apparatus, the dimensions are in the "millimeter" scale in terms of the diameters of the electrodes, the width of the antibody immobilization strips and the distances between detection electrodes. The concept also extends to electrochemical cells with much smaller dimensions. Smaller dimensions lead to advantages such as reduced sample volume and faster analysis times. An obvious extension is the "micrometer" scale for the above stated dimensions. Such electrochemical cells can be fabricated using standard microfabrication techniques with, for example, silicon and plastic technologies. At this dimension, biomaterial such as the capture antibody can be deposited in well-defined regions by miniature jets analogous to the ink jet technology used for printers, or other means. The concept is also extendable down into the "nanometer" scale using recently developed methodologies for depositing conducting materials with dimensions in this regime.

The cell in the drawing shows electrodes that are "wires or strips" with antibody immobilized as adjacent, parallel strips. Other geometrical relationships of electrode and immobilized capture agent could work equally well, or even better. For example, the capture agent could be immobilized as a spot and the detecting electrode by a surrounding ring. Or, the detecting electrode could be a disk directly opposite from the spot. In addition, it should be noted that the principle of spatial resolution demonstrated here for two analytes extends to an unlimited number of binding areas and associated electrodes, each for a different analyte.

It should be noted that although the demonstration of the concept is an immunoassay with a capture antibody, the invention applies to a wide range of analytical techniques that are analogous to immunoassay. For example, the antibody could be substituted with any capture agent. Examples are receptors, binding proteins, molecularly imprinted materials such as polymers. Any agent that "captures" the analyte with adequate selectivity for the intended application would work. Likewise other enzyme/substrate/product systems could be used as the labels for detection such as systems that produce peroxide as product, which is detectable by electrochemical methods.

Accordingly, the invention should be defined by the appended claims wherein we claim:

1. A simultaneous electrochemical assay device comprising a cell adapted to receive a sample, said cell having a surface having a plurality of analyte binding areas, each of said analyte binding areas having a different specific analyte binding substrate; and a plurality of working electrodes adapted to quantitatively measure enzymatic reaction product, each working electrode adjacent to one analyte binding area and separated from the nearest adjacent analyte binding area by a distance and a common reference electrode for said plurality of working electrodes wherein said device does not have means to mix a sample in said cell.

2. The device claimed in claim 1 wherein said binding substrates each comprise a plurality of different analyte specific proteins.

3. The device claimed in claim 1 wherein said binding substrates each comprise a different antigen.

4. The device claimed in claim 1 wherein said binding substrate comprises a different antibody.

5. The device claimed in claim 1 further comprising at least one auxiliary electrode in said cell.

6. The assay device claimed in claim 1 wherein said device has a common reference electrode for said plurality of working electrodes.

* * * * *